US006555659B1

(12) United States Patent
Ayers et al.

(10) Patent No.: US 6,555,659 B1
(45) Date of Patent: Apr. 29, 2003

(54) PROCESS FOR ISOLATING GLYCOMACROPEPTIDE FROM DAIRY PRODUCTS WITH A PHENYLALANINE IMPURITY OF 0.5% W/W

(76) Inventors: John Stephen Ayers, Palmerston North (NZ); Kay Patricia Coolbear, Palmerston North (NZ); David Francis Elgar, Palmerston North (NZ); Mark Pritchard, Fitzherbert West Palmerston North (NZ)

( * ) Notice: Subject to any disclaimer, the term of this patent is extended or adjusted under 35 U.S.C. 154(b) by 0 days.

(21) Appl. No.: 09/625,043

(22) Filed: Jul. 24, 2000

Related U.S. Application Data (63) Continuation of application No. 09/269,918, filed as application No. PCT/NZ97/00125 on Oct. 1, 1997, now abandoned.

(30) Foreign Application Priority Data

Oct. 1, 1996 (NZ) ................................................ 299483

(51) Int. Cl.[7] ............................ C07K 14/00; A23J 1/20
(52) U.S. Cl. ...................... 530/395; 530/322; 530/360; 530/361; 530/412; 530/414; 530/416; 530/418; 530/832; 530/833
(58) Field of Search ................................. 530/395, 392, 530/360, 361, 412, 414, 416, 418, 832, 833

(56) References Cited

U.S. PATENT DOCUMENTS

| | | | |
|---|---|---|---|
| 4,042,575 A | 8/1977 | Eustache | 530/395 |
| 4,042,576 A | 8/1977 | Eustache | 530/395 |
| 5,075,424 A | 12/1991 | Tanimoto et al. | 530/361 |
| 5,968,586 A | 10/1999 | Etzel | 426/657 |

FOREIGN PATENT DOCUMENTS

| | | |
|---|---|---|
| AU | 74081/91 | 4/1991 |
| EP | 0 291 264 A2 | 5/1988 |
| GB | 2 188 526 A | 2/1986 |
| GB | 2 251 858 A | 1/1992 |
| JP | 04243898 A | 8/1992 |
| WO | WO/9317581 | 9/1993 |
| WO | WO/9415952 | 7/1994 |

OTHER PUBLICATIONS

S.C. Marshall, "Casein Macropeptide From Whey—A New Product Opportunity," Food Research Quarterly, vol. 51, Nos. 1 & 2, 1991, pps. 86–91.
Morimasa Tanimoto, Yoshihiro Kawasaki, Shun'ichi Dosako, Kenkicih Ahiko, and Ihciro Nakajima, "Large–scale Preparation of κ–Casein Glycomacropeptide from Fennet Casein Whey,", Biosci. Biotec. Biochem., 56 (1), 140–141, 1992.

(List continued on next page.)

Primary Examiner—Christopher S. F. Low
Assistant Examiner—Abdel A. Mohamed
(74) Attorney, Agent, or Firm—Knobbe, Martens, Olson & Bear, LLP (57) ABSTRACT

The present invention is related to a method for the purification of glycomacropeptide (GMP) with an amino acid composition containing no greater that 0.5% (w/w) phenylalanine, comprising the steps of contacting a GMP-containing feedstock with a first anion exchanger under conditions to adsorb the GMP, eluting the adsorbed GMP from the anion exchanger and removing impurities from the GMP-containing eluate by either: (i) contacting the GMP-containing eluate with a cation exchanger in conditions under which the impurities in the eluate are adsorbed onto the cation exchanger, or (ii) precipitating the impurities in GMP-containing eluate using conditions in which the GMP remains i solution, or (iii) contacting the GMP-containing eluate with a second anion exchanger in conditions under which the impurities in the eluate are adsorbed onto the anion exchanger, and recovering the GMP from whichever one or more of the steps (i), (ii) or (iii) was used.

43 Claims, 3 Drawing Sheets

OTHER PUBLICATIONS

M. Outinen, O. Tossavainen, E.-L. Syvaoja and H. Korhonen, "*Chromatographic isolation of κ–casein macropeptide from cheese whey with a strong basic anion exchange resin,*" Milchwissenschaft 50 (10) 1995, pps. 570–574.

Y. Kawasaki, H. Kawakami, M. Tanimoto, S. Dosako, A. Tomizawa, M. Kotake and I. Nakajima, "*pH–Dependent molecular weight changes of κ–casein glycomacropeptide and its preparation by ultrafiltration,*" Milchwissenschaft 48 (4), 1993, pps. 191–195.

H. Kawakami, Y. Kawasaki, S. Dosako, M. Tanimoto and I. Nakajima, "*Determination of κ–casein glycomacropeptide by high performance liquid chromatography without trichloroacetic acid pretreatment,*" Milchwissenschaft 47 (11), 1992, pps. 688–693.

G.W. Smithers, R.S. Bradford, G.O. Regester and R.J. Pearce, "*New casein protein products for the food industry,*" Food Australia 43 (6), Jun. 1991, pps. 252–254.

L. Chu, A. MacLeod and L. Ozimek, "*Isolation of glycomacropeptide from sodium caseinate hyrdolysate solution by ultrafiltration,*" Milchwissenschaft 51 (6), 1996, pps. 303–306.

Solange Soulier, Bruno Ribadeau–Dumas and Robert Denamur, "*Purification des caseines κde brebis,*" European Journal of Biochem., 50, 1975, p. 445.

Tadao Saito, Atsuo Yamaji and Takatoshi Itoh, "*A New Isolation Method of Caseinogycopeptide from Sweet Cheese Whey,*" Journal of Dairy Science 74, 1991, pps. 2831–2837.

PROCESS FOR ISOLATING GLYCOMACROPEPTIDE FROM DAIRY PRODUCTS WITH A PHENYLALANINE IMPURITY OF 0.5% W/W

This application is a Continuation of application Ser. No. 09/269,918, filed Apr. 1, 1999, now abandoned, which is the U.S. National Phase under U.S.C. §371 of International Application PCT/NZ97/00125, filed Oct. 1, 1997.

TECHNICAL FIELD

This invention relates to a process for isolating glycomacropeptide (GMP) from a feedstock. More particularly, it relates to the isolation of GMP to a purity under which it has an amino acid composition containing less than 0.5% w/w of phenylalanine (Phe).

GMP is one of a number of names for the peptide split off from κ-casein by the enzymes chymosin and/or pepsin. The peptide is also known as casein macropeptide (CM) or casein derived peptide (CDP).

GMP is found in sweet wheys. GMP carries all of the carbohydrate groups of the parent κ-casein protein. κ-casein is the only casein protein which is glycosylated. Another feature is that when the pH of a solution of GMP is less than 4 the molecular weight is 9000 Da. When the pH is greater than 4, the GMP apparent molecular weight increases to 45000 Da. When concentrating solutions of GMP by ultrafiltration it is preferable for the solution to have a pH>4 unless the membrane cut-off is ≦10,000 Da. A further feature of GMP is that it does not contain any aromatic amino acids including Phe in its structure.

GMP has a number of potential therapeutic uses as well as having functional properties which make it very useful as an ingredient in food compositions. One important utility is as a nutritional component for use in the diets of persons suffering from phenylketonuria (PKU) (Marshall S, (1991), Food Res Quarterly, 51, 86–91). Phenylketonurics lack Phe hydroxylase in their metabolic system. Therefore, they are unable to utilise Phe present in foods. This can result in a sufficient accumulation of Phe to cause irreversible mental retardation. In order for GMP to be safe for use in feeding to phenylketonurics the Phe level should be as low as possible. A representative product specification would require that the Phe level be 0.5% w/w or less and it would be desirable to have a method of isolating GMP to such a low level of Phe impurity on a production level scale.

BACKGROUND ART

Although a number of processes for isolating GMP are known, none of those processes have been shown to be capable of producing GMP having 0.5% w/w or less Phe impurity on a production level scale. One reason for this is that a GMP product of sufficient purity has not yet been manufactured. For example, assuming that the contaminant proteins contain an average 4% Phe, then a purity of greater than 88% GMP is required to give less than 0.5% Phe.

For example, EP A291264 discloses an industrial scale process for the purification of GMP from a mixture of α, β and κ caseins whereby the caseins are subjected to enzymatic milk-coagulating treatment to obtain non-coagulate components as an effluent. The effluent is then kept or rendered acidic to form a precipitate and the remaining effluent subjected to a desalting treatment to produce a GMP with 82% purity. No amino acid analysis data of the purified GMP is disclosed. This process is further described in Tanimoto et al, Biosci. Biotech. Biochem., 56(1), 140–141, 1992, which discloses a large-scale preparation of GMP from rennet casein whey. The whey was filtered and the filtrate desalinated and freeze dried to produce GMP powder having a Phe content of 2.4% w/w. The GMP powder was further purified by Q-Sepharose® ion-exchange chromatography to give a purified GMP with 0.9% w/w Phe.

GB 2188526 discloses a process for producing a proteinaceous material from milk or casein-containing milk products at pH 4–6 using anion exchange chromatography. No amino acid analysis data of the purified proteinaceous material is disclosed.

GB 2251858 discloses a process for producing GMP from milk raw materials by adjusting the pH of the material to ≦4, contacting the solution with an anion exchanger, concentrating and desalinating the eluate to give a GMP a 51% purity. This product may be further purified by ultrafiltration according to U.S. Pat. No. 5,075,424 (below) to produce GMP of 87% purity. No amino acid analysis data of the purified GMP is disclosed.

Outinen et al, Milchwissenschaft 50(10), 570–574, 1995, discloses a process for isolating GMP from cheese whey using an inexpensive polystyrenic strong basic anion exchange resin at pH 5. The Phe content of the purified GMP was 0.9% w/w. Further purification of this product by TCA precipitation gave a Phe content of 0.63–0.79% w/w.

U.S. Pat. No. 5,075,424 discloses a process for producing GMP from milk starting materials at pH≦4 by ultrafiltration. This process relies on the discovery that GMP has a smaller apparent molecular weight at pH<4 than at pH>4 so that only GMP will pass through a 10,000–50,000 molecular weight cut off membrane at pH<4. After ultrafiltration, the pH of the permeate is adjusted to pH≧4 and subjected to a second ultrafiltration using a membrane with a molecular weight cut-off of ≦50,000 Da to give a GMP retentate which is 82% pure. No amino acid analysis data of the purified GMP is disclosed.

Kawasaki et al, Milchwissenschaft 48(4), 191–195, 1993 discloses a purified GMP product using the method of U.S. Pat. No. 5,075,424 having a Phe content of 0.6% w/w and a purity of 81%.

Kawasaki et al, Milchwissenschaft 47(11), 688–693, 1992 discloses the same GMP product as above which is fractionated further by analytical chromatography systems (size exclusion chromatology and anion exchange chromatography). The purified GMP products had Phe content of 0.1–0.3%. However, such analytical systems are not suitable for mass production.

U.S. Pat. Nos. 4,042,575 and 4,042,576 each disclose a process of purifying glycoproteins (including GMP) by double ultrafiltration or flocculation of whey proteins followed by ultrafiltration. No amino acid analysis data for the purified glycoproteins is disclosed.

JP 04243898 discloses a process for producing GMP from cheese whey etc at pH 3–6 by heating, adding ethanol, centrifuging and loading the supernatant onto an anion exchange column and eluting GMP with 0.3M ammonium bicarbonate. This process is also reported in J. Dairy Sci 74, 2831–2837, 1991, where amino acid analysis data is given for the isolated GMP. However, Phe is not included in their analysis.

AU 74081/91 discloses a process for producing GMP from a whey protein concentrate in which the proteins are flocculated, the supernatant concentrated by ultrafiltration and the retentate treated with ethanol to produce a precipitate and a second supernatant. The second supernatant is collected and dried to give GMP powder of 84% purity. No amino acid data is disclosed.

JP 3-294299 discloses a process for the manufacture of GMP from whey by heating a 5–50 wt% solution of whey proteins followed by freezing and thawing. The supernatant is then separated, desalted and concentrated by ultrafiltration. No purity or amino acid analysis data of the recovered GMP is given.

WO 94/159252 discloses a method of producing GMP from whey using ultrafiltration, heat treatment of the retentate at 95° C. for 15 minutes, adjustment of the pH to 4–5 filtering and collecting GMP from the filtrate. The GMP is 70% pure and the Phe content is ⅓ that of the raw material. The exact concentration of Phe is not disclosed.

EP 0488589 discloses a process for producing GMP by contracting milk raw materials with an ion exchanger, collecting the protein which does not adsorb on the ion exchanger, concentrating and desalting to obtain GMP of 55%–88% purity. No amino acid analysis data is provided.

All of the aforementioned processes are aimed at producing enriched GMP fractions and are not necessarily concerned with reducing Phe content of the GMP as they are not concerned with producing diets for phenylketonurics.

According to WO 93/17587, Phe may be removed from proteinaceous material such as whey protein by enzyme hydrolysis and ultrafiltration to remove unhydrolysed protein. The permeate containing mainly amino acids and small peptides is passed through a column of adsorption resin to remove Phe at pH 6–7 (to give a product with 0.3% Phe) or pH 3–5 (to give a product with ≦0.1% Phe). Methods involving enzymatic hydrolysis of proteins such as this one cannot be used to purify GMP since they would degrade it to low molecular weight fractions. They are thus not suitable for producing purified GMP.

Smithers W et al. Food Australia 43(6), June 1991, 252–254 outlines a method of isolating GMP (CDP) from cheese or rennet casein whey by selective adsorption at pH 5 using an anion exchanger. Non-bound proteins are then washed out of the exchanger using water and the GMP eluted with mild acid. The eluate is microfiltered to remove a contaminant and subsequently concentrated by ultrafiltration and dried to give a GMP powder stated to have >90% purity but no Phe analysis data is given.

The present invention provides alternative methods of producing purified GMP having 0.5% w/w or less Phe impurity on a production level scale.

SUMMARY OF THE INVENTION

It is therefore an object of this invention to go some way towards achieving this desideratum or at least to offer the public a useful choice.

Accordingly, the invention may be said broadly to consist in a process for the purification of GMP characterised in that the purified GMP has a Phe content of not greater than about 0.5% (w/w) which comprises:

contacting a GMP containing feedstock with a first anion exchanger under conditions to adsorb said GMP, eluting said adsorbed GMP from said anion exchanger and removing impurities from said GMP containing eluate by either:
  i) contacting said GMP containing eluate with a cation exchanger in conditions under which said impurities in said eluate are adsorbed onto said cation exchanger, or
  ii) precipitating said impurities in said GMP containing eluate using conditions by means of which said GMP remains in solution, or
  iii) contacting said GMP containing eluate with a second anion exchanger in conditions under which said impurities in said eluate are adsorbed onto said anion exchanger and, recovering said GMP from whichever one or more of said steps (i), (ii) or (iii) was used.

In one alternative said conditions in said first anion exchanger are such that said GMP is adsorbed selectively.

In another alternative said conditions in said first anion exchanger are such that both said GMP and other whey proteins in said feedstock are adsorbed and then said first anion exchanger is eluted under conditions which selectively elute said whey proteins and then elute GMP.

Preferably said condition for eluting said whey proteins or said impurities is obtained by adjusting said first anion exchanger to a pH of 4–5 if necessary and then using an appropriate eluent such as 20–60 mM sodium chloride.

The whey protein in the eluate may optionally be recovered as an additional product.

Preferably the feedstock for said first anionic exchanger is a cheese or rennet whey, an ultrafiltration (UF) retentate or a whey protein concentrate produced from a cheese or rennet whey or a whey protein isolate produced from one of these by an anion exchanger.

Alternatively said feedstock has been pretreated to remove substantially all the whey proteins contained therein except GMP.

Preferably said whey proteins have been removed by either heat treating said feedstock or contacting it with a cation exchanger.

In a further alternative said feedstock is derived from a casein or caseinate product prepared by acid precipitation and has been treated with a suitable enzyme to release GMP in solution and precipitate casein.

In one embodiment said GMP containing eluate from said first anionic exchanger is treated by said alternative (i).

In a second embodiment said GMP containing eluate from said first anionic exchanger is treated with said alternative (ii).

In a third embodiment said GMP containing eluate from said first anionic exchanger is treated with said alternative (iii).

In another alternative said GMP containing eluate from said first anionic exchanger is treated with said alternative (i) followed by treatment with said alternative (ii).

In another alternative said GMP containing eluate from said first anionic exchanger is treated with said alternative (ii) followed by treatment with said alternative (i).

In another alternative said GMP containing eluate from said first anionic exchanger is treated with said alternative (i) followed by treatment with said alternative (iii).

In a still further alternative said GMP containing eluate from said first anionic exchanger is treated with said alternative (iii) followed by treatment with said alternative (i).

Preferably said GMP containing feedstock is contacted with said first anionic exchanger at a pH between 3 and 9. More preferably, said pH is between 3.5 and 5.

In one alternative said eluent for desorbing said GMP from said first anionic exchanger contains salt in a sufficient quantity to make the solution approximately 20–200 mM and acid in a sufficient quantity to lower the pH to 2–3.

In another alternative said eluent for desorbing said GMP from said first anion exchanger contains salt in a sufficient quantity to make the solution about 175 mM and base in sufficient quantity to raise the pH to about 8 to 9.

Preferably, said GMP containing eluate in alternative (i) is contacted with said cation exchanger at a pH between about 1.5 and about 4.5 and at a salt concentration of up to 100 mM.

Preferably said salt is sodium chloride.

Preferably said GMP is neutralised, concentrated by ultrafiltration and/or diafiltration prior to drying.

Preferably in said alternative (ii) said conditions are pH 3.5–4.5 attained by adding an acid or base to the GMP containing eluate.

Preferably said acid is hydrochloric acid.

Preferably said base is sodium hydroxide.

Preferably after said precipitation step the mixture is centrifuged or microfiltered and the supernatant or permeate is either further processed according to alternative i) or is immediately neutralized, concentrated and dried to produce a GMP powder.

Preferably, in said alternative iii) said second anion exchanger is substituted with amino groups bearing a hydrophobic group. Preferably, said hydrophobic group is selected from the group consisting of $C_6$–$C_{12}$ hydrocarbon groups including aromatic hydrocarbons. Preferably said hydrophobic group is a $C_8$ hydrocarbon group.

Preferably, the GMP loaded first anion exchanger in the initial step is washed with a dilute salt solution, such as 50 mM sodium chloride, prior to said GMP elution to remove impurities therefrom.

Preferably in said alternative iii), said GMP containing eluate is adjusted to a salt concentration of 125–200 mM with a physiologically acceptable salt and the pH is at least 7.

Preferably the non-adsorbed GMP passing through said second anion exchanger is either further processed according to alternative i) or is immediately neutralised, concentrated by ultrafiltration and/or diafiltration and dried.

In one alternative the GMP from the initial stage or alternative i) is concentrated by ultrafiltration before conducting alternative ii) or iii).

Preferably the process is conducted under conditions which promote a high yield.

In another alternative the invention may be said broadly to consist in a process for the purification of GMP to a Phe content of not greater than about 0.5% (w/w) which comprises:

contacting a GMP feedstock with an anion exchanger under conditions to adsorb selectively said GMP, and eluting selectively said adsorbed GMP from said anion exchanger leaving impurities on said anion exchanger, and recovering GMP from the GMP containing eluate.

In this alternative, these conditions are used to selectively desorb said GMP from the anion exchanger leaving impurities on said anion exchanger in a single step by combining the initial step with alternative (iii).

Preferably said GMP loaded first anion exchanger in the initial step is washed with a dilute salt solution, such as 50 mM sodium chloride, prior to said GMP elation to remove impurities therefrom.

Preferably said anion exchanger is regenerated by eluting said impurities therefrom after said GMP elution.

Preferably said GMP is selectively eluted with an eluent having a pH of about 8–9 and a salt concentration of about 175 mM.

The invention may also be said broadly to consist in a method of purifying GMP from a GMP feedstock substantially as herein described with reference to FIG. 1 of the accompanying drawings and by reference to any example thereof.

The invention may also be said broadly to consist in GMP purified to contain no more than 0.5% w/w of Phe whenever prepared by a process as defined herein.

More preferably the invention may be said broadly to consist in GMP purified to contain no more than 0.4% Phe whenever prepared by a process as defined herein.

This invention may also be said broadly to consist in the parts, elements and features referred to or indicated in the specification of the application, individually or collectively, and any or all combinations of any two or more of said parts, elements or features, and where specific integers art mentioned herein which have known equivalents in the are to which this invention relates, such known equivalents are deemed to be incorporated herein as if individually set forth.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENT

Figure 1:
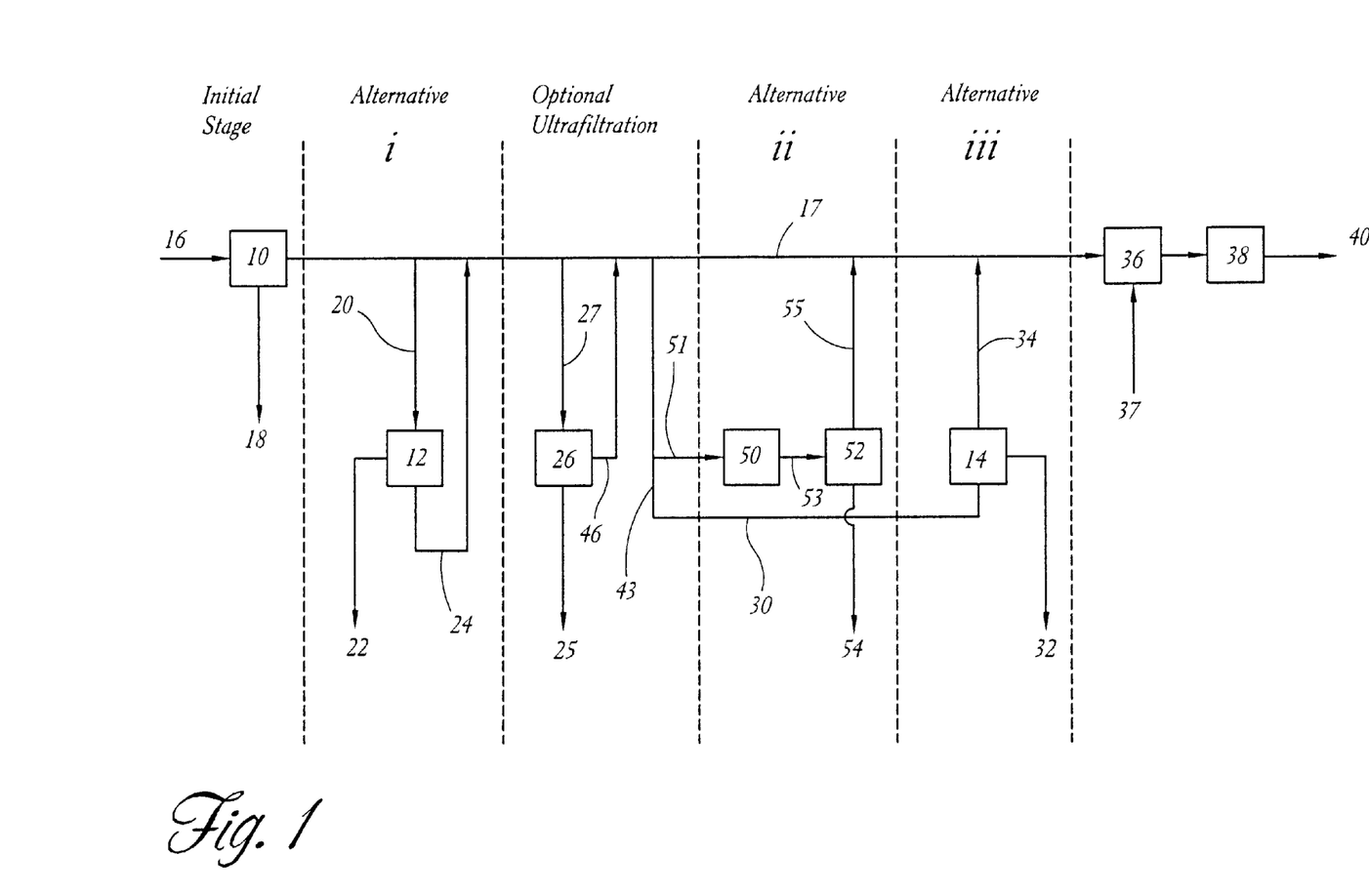
FIG. 1 is a flow diagram showing the various alternative processes which may be used to purify GMP according to the invention.

FIG. 1 shows some of the ways in which alternative methods according to the invention may be combined before producing the final GMP powder as illustrated in the following examples.

In an initial stage of GMP purification a GMP feedstock 16 is contacted with a first anion exchanger 10. Whey proteins (other than GMP) 18 are not adsorbed by the exchanger 10 and are removed after the required contacting time. GMP in the eluate is then removed via line 17 from the anion exchanger 10 which is washed and prepared for another cycle of GMP adsorption.

Eluate in line 17, in one alternative, is fed along feed line 20 into cation exchanger 12. In this case the conditions are adjusted so that impurities are adsorbed and the GMP passes through the cation exchanger 12 along feed line 24 back to line 17 where it is neutralised and passed to an ultrafilter 36 which may be subjected to diafiltration with liquid 37. The retentate is then dried in the drier 38 to produce GMP powder 40. Impurities are eluted from cation exchanger 12 along with eluate 22. This is referred to as alternative (i) in FIG. 1.

In another alternative the eluate containing GMP in line 17 is passed to feed line 27. In one embodiment the pH of the solution in feed line 27 is adjusted to ≧4 and subjected to ultrafiltration in the ultrafilter 26 and the permeate 25 is discarded. The retentate is passed through lines 46, 17, 43 and 51 to a precipitation vessel 50 and adjusted to about pH 4 by the addition of acid or base. The mixture is then passed along feed line 53 to centrifuge or microfilter 52. The supernatant or permeate in line 55 is neutralised and returned to line 17 and treated as described above for alternative (i) to produce GMP powder 40. The precipitate or retentate 54 is discarded. In another embodiment the solution from line 17 is fed along lines 43 and 51 directly to the precipitating chamber 50. This is referred to as alternative (ii) in FIG. 1.

Alternatively, the GMP containing solution from feed line 17 may be fed along lines 43 and 30 into a second anion exchanger 14. The conditions in the second anion exchanger are such that the GMP containing solution passes through and the impurities are adsorbed. In an alternative the GMP containing solution is first diverted from line 17, along line 27, neutralised and passed into an ultrafilter 26. The permeate 25 is discarded. The concentrated retentate from line 46 is passed along lines 17, 43 and 30 into the anion exchanger 14. The GMP containing solution from second anion exchanger 14 is passed along lines 34 and 17 to ultrafilter 36 which may be subjected to diafiltration with the diafiltration liquid 37. The retentate is then dried in dryer 38 to produce a GMP powder 40. The adsorbed impurities in anion exchanger 14 are eluted and discarded in eluate 32. This is identified as alternative iii) in FIG. 1 of the process.

Although the above descriptions indicate the preferred order in which purification steps may be used, they can be used in any order.

Example 1—Comparative

A cheese whey WPC powder (sold under the trade mark "ALACEN 392™") containing 80% protein was reconstituted at 10% (w/w) solids (GMP concentration 14.2 mg/mL). The pH of this was adjusted sequentially to pH 5.3, 5.1, 4.9, 4.7, 4.2, 4.0 and 3.7 using 5 M hydrochloric acid. At each pH a 50 mL sample was removed and added to 23 g (33 mL) of anion exchanger (QA GibcoCel, batch no. 1564 (Q2-H), Life Technologies Ltd, New Zealand)$^a$ stirred for 40 minutes at room temperature while holding the pH constant with 1 M sodium hydroxide. The anion exchanger was then collected on a sintered glass filter, drained and washed with water. The filtrate and washings were combined and made up to 75 mL for analysis of residual GMP by HPLC using a Mono S® (Pharmacia)$^b$ column. The anion exchanger was transferred to a beaker to which was then added water, 5 M sodium chloride (1 mL) and 5 M hydrochloric acid to give a total volume of 50 mL at pH 2. This was stirred for an hour after which time the exchanger was again collected on the filter, drained and washed with water to give a total volume of 60 mL of eluate (combined filtrate and washings). This was analysed for GMP, α-lactalbumin and β-lactoglobulin by HPLC using ion exchange (Mono S®)$^b$ and gel filtration (Superdex™ 75, Pharmacia)$^c$ columns. The solutions of desorbed protein were neutralized, dialysed and freeze-dried. Samples of these were hydrolysed in 6 M hydrochloric acid at 110° C. for 23 hours and 110° C. analysed for amino acid composition. The % Phe values given herein are as a % of the total amino acids determined in the hydrolysate.

$^a$GibcoCel Ion Exchange Matrices are a family of cellulose-based industrial ion exchange chromatography resins designed for large-scale protein separation applications. These matrices are prepared by a patented cross-linking process that significantly increases the porosity and improves the durability of the matrix. QA(E)—quaternary amino-ethyl: a strong anion exchange resin, fully ionized over a wide pH range (2–12). SP—sulphopropyl: a strong cation exchange resin, fully ionized over a wide pH range (2–12).
$^b$MonoBeads® is a beaded hydrophilic resin with an extremely narrow particle size distribution, 10 μm, d<=0.3 μm. The base matrix is substituted with quaternary amine groups to produce Mono Q®, with sulphonic acid groups to yield Mono S®. Mono Q® is a strong anion exchanger which binds negatively charged biomolecules. The positively charged quaternary amine groups remain equally charged over the entire useful pH range of 3–11. Mono Q® is especially useful in the isolation of oligonucleotides and monoclonal antibodies. Mono S® is a strong cation exchanger which binds positively charged biomolecules. The negatively charged sulphonic groups remain equally charged over the entire useful pH range of 3–11. Mono S® is especially useful for the separation of peptides at lower pH.
$^c$Superdex™ 75 is excellent for separating monomeric and dimeric forms of lower molecular weight recombinant proteins and peptides. Separation range (M$_r$): 3,000–70,000 globular protein. Matrix—spherical composite of cross-linked agarose and dextran, average particle size—13 μm, stable in all common buffers: 1 M acetic acid, 8 M urea, 6 M guanidine hydrochloride, 30% isopropanol, 70% ethanol, 1 M NaOH (for cleaning in place), pH stability 3–12 (long term), 1–14 (short term).

Figure 2:
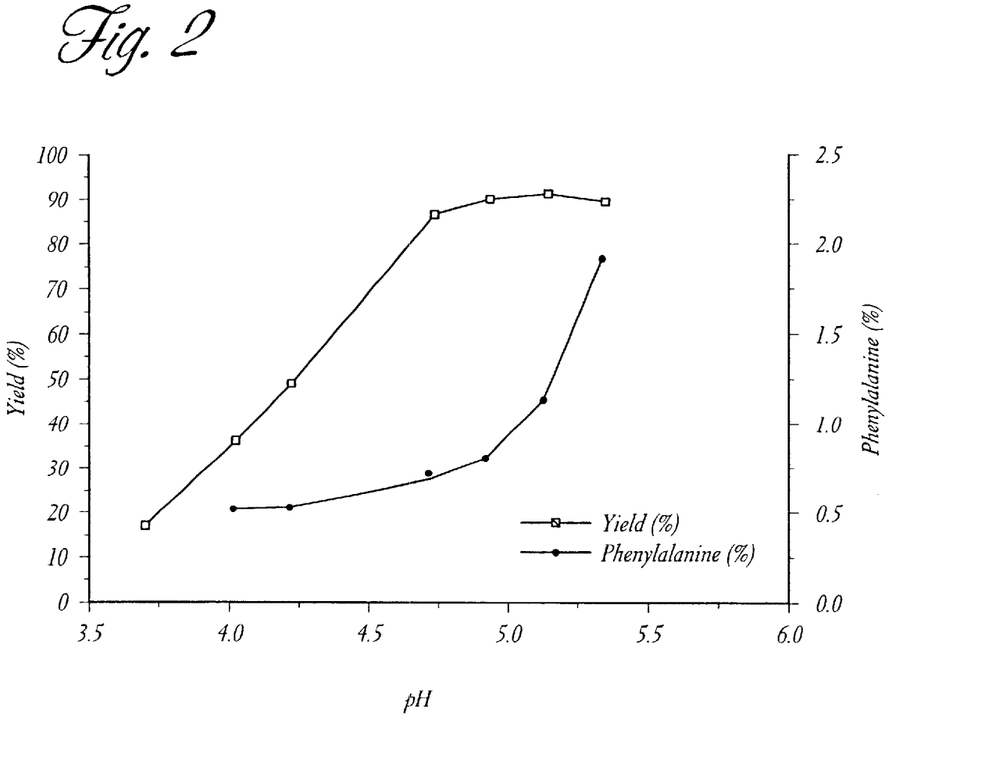
FIG. 2 is a plot of yield and purity of GMP against pH showing the effect of pH of the GMP adsorption on the yield of GMP and its Phe value.

The results are given in Tables 1 and 2 and FIG. 2. They show the difficulty of obtaining by ion exchange a GMP product with greater than 88% purity and an amino acid composition with less than 0.5% Phe. This is particularly true using conditions which also favor a high yield of GMP.

TABLE 1

Recovery of GMP from Cheese Whey WPC

| | pH of protein adsorption | | | | | | |
|---|---|---|---|---|---|---|---|
| | 3.7 | 4.0 | 4.2 | 4.7 | 4.9 | 5.1 | 5.3 |
| GMP unadsorbed (%) | 76 | 60 | 49 | 12 | 6 | 2 | 1 |
| GMP eluted (%) | 17 | 36 | 49 | 86 | 90 | 91 | 89 |
| GMP accounted for (%) | 93 | 96 | 98 | 98 | 96 | 93 | 90 |
| Phe (% of total amino acids) | — | 0.52 | 0.53 | 0.69 | 0.82 | 1.15 | 1.93 |

TABLE 2

Protein Composition of Products (%)

| | pH of protein adsorption | | | | |
|---|---|---|---|---|---|
| | 4.0 | 4.7 | 4.9 | 5.1 | 5.3 |
| GMP$^1$ | 86.8 | 82.6 | 78.8 | 68.9 | 46.4 |
| α-lactalbumin$^2$ | 1.9 | 3.7 | 3.7 | 4.2 | 3.8 |
| β-lactoglobulin$^2$ | 1.0 | 1.8 | 4.4 | 12.8 | 27.8 |
| Other$^3$ | 10.3 | 12.0 | 13.1 | 14.1 | 22.0 |

$^1$Concentration in eluate measured using a Mono S ® column.
$^2$Concentration in eluate measured using a Superdex ™ 75 column.
$^3$Calculated from the % Phe in the amino acid composition of the final product on the basis of the Phe content of α-lactalbumin and β-lactoglobulin being 4.2 and 3.2% respectively and assuming an average value of 4% Phe for the unidentified impurities.

EXAMPLE 2

A WPC powder (ALACEN 392™) manufactured from cheese whey was reconstituted at 10% (w/w) solids. The pH of this was adjusted to 4.9 with 5 M hydrochloric acid and 1 liter of it mixed for 40 minutes at room temperature with 460 g (660 mL) of washed and drained anion exchanger (QA GibcoCel) while maintaining the pH at 4.9. This mixing was carried out in a vessel fitted with stirrer and a screen across the bottom. At the end of the mixing period the anion exchanger was drained and washed with water.

Water was added to the drained anion exchanger to give a total volume of 1 liter, Sodium chloride (20 mL of 5 M) was added to make the solution approximately 100 mM, and the pH was lowered to 2.0 with 5 M hydrochloric acid. This was mixed for 1 hour at room temperature to desorb GMP and other protein from the exchanger and then drained and the exchanger washed with water to give 1 liter of GMP solution (filtrate and washings) at about pH 2 and 100 mM sodium chloride. The anion exchanger was then ready for use again. A 10 mL sample of the GMP solution was removed, neutralized, dialysed and freeze-dried for Phe analysis. The remainder was passed through a 125 nmL column of cation exchanger (SP GibcoCel) which had been previously stirred and adjusted to pH 2 prior to settling and packing as a column. The flow rate was 8 mL/min. The last of the protein solution was flushed through the column with 125 mL of water. The column breakthrough and washings were collected and combined to give a total volume of 1.125 L of semi-purified GMP. HPLC analysis using a Mono Q® column showed that α-lactalbumin, β-lactoglobulin and other material had been removed from the GMP. A 10 mL sample of this GMP solution was removed, neutralized, dialysed and freeze-dried for Phe analysis.

The GMP solution was made 200 mM in sodium chloride by the addition of a further 25 mL of 5 M sodium chloride and the pH adjusted to 8.5 with 2 M sodium hydroxide. This was then passed through a 140 mL column of QA GibcoCel anion exchanger which had been previously stirred in 200 mM sodium chloride and adjusted to pH 8.5 prior to settling and packing as a column. A flow rate of 10 mL/min was used. The last of the protein solution was flushed through the column with 200 mM sodium chloride. The column breakthrough and washings were collected and combined to give 1.4 liters of purified GMP which was neutralized with 5 M hydrochloric acid. A sample (10 mL) was dialysed and freeze-dried for Phe analysis. The rest was concentrated by ultrafiltration, diafiltration and freeze dried.

Analysis of the crude, semi-purified and purified GMP solutions by UV absorption at 214 nm showed that 83% of the 214 nm absorbing material passed through the SP and QA columns. Much of that lost can be attributed to impurities so that the recovery of GMP through alternatives (i) and (iii) was >83%. The Phe contents of the GMP samples taken at each of the three stages of the recovery and purification process were as follows.

| | | |
|---|---|---|
| Initial Stage | Protein desorbed from QA GibcoCel column | 0.97% Phe |
| Alternative i) | Breakthrough from SP GibcoCel column | 0.55% Phe |
| Alternative iii) | Breakthrough from QA GibcoCel column | 0.38% Phe |

EXAMPLE 3

This was the same as Example 2 except that the GMP was desorbed from the first anion exchanger at pH 2 in 75 mM sodium chloride which was then passed through the cation exchange column. This column passed solution (breakthrough solution) of GMP (1.12 liters) was made up to only 175 mM in sodium chloride by the addition of 26 mL of 5 M sodium chloride prior to passage through the second anion exchange QA GibcoCel column (140 mL) at pH 8.5.

The Phe results were as follows:

| | | |
|---|---|---|
| Initial Stage | Protein desorbed from QA GibcoCel column | 1.0% Phe |
| Alternative i) | Breakthrough from SP GibcoCel column | 0.48% Phe |
| Alternative iii) | Breakthrough from QA GibcoCel column | 0.16% Phe |

The overall yield of purified GMP was 70% of the GMP in the WPC powder.

The amino acid compositions of the purified GMP and the theoretical value calculated from the primary structures of the A and B variants (1:1) were as follows:

TABLE 3

AMINO ACID COMPOSITION OF PURIFIED GMP

| Amino Acid | Theoretical value (%) | Experimental Value (%) |
|---|---|---|
| Asx | 7.6 | 8.28 |
| Thr | 17.5 | 16.58 |
| Ser | 8.1 | 7.21 |
| Glx | 18.8 | 19.66 |
| Pro | 11.8 | 11.41 |
| Gly | 1.0 | 0.98 |
| Ala | 6.3 | 5.31 |
| Cys | 0 | 0.00 |
| Val | 9.0 | 8.66 |
| Met | 1.9 | 2.73 |
| Ile | 10.9 | 10.73 |
| Leu | 1.7 | 2.50 |
| Tyr | 0 | 0.08 |
| Phe | 0 | 0.16 |
| His | 0 | 0.11 |
| Lys | 5.6 | 5.32 |
| Arg | 0 | 0.29 |
| Trp | 0 | 0.0 |

EXAMPLE 4

WPC powder (180 g of ALACEN 392™) manufactured from cheese whey was reconstituted at 10% solids (w/w) to give 1.8 kg of solution. It was adjusted to pH 4.8 with 2 M sulphuric acid and mixed with 800 g (1.15 L) of QA GibcoCel anion exchanger at pH 4.8 for 40 minutes at room temperature. The GMP-depleted WPC was then drained from the anion exchanger and the latter washed with water and then resuspended in further water to give a total volume of 1.8 L. This was made approximately 75 mM in sodium chloride by the addition of 27 mL of 5 M sodium chloride, the pH adjusted to 2.0 with 5 M hydrochloric acid and then stirred for 1 hour at room temperature to desorb the GMP. This was drained from the anion exchanger which was washed with water to give 1.8 kg of solution of GMP, pH 2.0 and 75 mM in sodium chloride.

This GMP solution was passed through a 175 mL column of SP GibcoCel at pH 2 and followed by 175 mL of water. The flow rate was 15 mL/min. The first 100 mL of breakthrough from the column was discarded and the remaining 1.875 kg of breakthrough and wash water collected and neutralized to pH 7. Most of this semi-purified GMP solution was heated to 50EC and concentrated 5–6 fold by ultrafiltration using an Amicon spiral wound membrane cartridge (S1YM10) with a 10,000 molecular weight cut-off. Samples of the retentate were further treated in two different ways.

(a) Acidification and clarification

The retentate (10 mL) was acidified to pH 4 with 5 M hydrochloric acid and left to stand while some of the precipitated impurities agglomerated. These were removed by centrifugation. The supernatant was neutralized, dialysed and freeze-dried.

(b) Anion exchange column

The retentate (11 mL) was made up to 170 mM by the addition of 0.22 mL of 5 M sodium chloride and shifted to pH 8.0 with 2 M sodium hydroxide. This was then passed through a 8 mL column of QA GibcoCel anion exchanger over 1 hour and flushed through the column with 16 mL of 170 mM sodium chloride. The combined breakthrough and column washings were neutralized, dialysed and freeze-dried.

For comparative purposes a 65 mL sample of the unconcentrated semi-purified GMP was made up to 170 mM sodium chloride, pH 8 adjusted and passed through another 8 mL column of QA GibcoCel anion exchanger over 2 hours.

The Phe analyses gave the following results:

| | | |
|---|---|---|
| Alternative i) | Prior to UF | 0.51% Phe |
| | Post UF | 0.55% Phe |
| Alternatives i) and ii) | After UF and precipitation of impurities at pH 4 | 0.29% Phe |
| Alternatives i) and iii) | Final purification by QA GibcoCel column. | |
| | With prior UF | 0.30% Phe |
| | Without prior UF | 0.33% Phe |

These results show that precipitation at about pH 4 (alternative ii) may be used to remove impurities as an alternative to passage through an anion exchange column at pH 8–9 (alternative iii).

The amount of Phe containing impurities removed by this method was found to depend on the concentration of the solution and its pH. The impurities are partially soluble at pH 3–4.5, and soluble outside this range. Their removal by precipitation is thus aided by concentration by ultrafiltration prior to adjusting to pH 4.

EXAMPLE 5

A WPC powder (ALACEN 392™) manufactured from cheese whey was reconstituted at 10% solids. The pH of this was adjusted to 4.75 with 5 M hydrochloric acid and 1 liter of it mixed with 460 g (660 mL) of washed and drained QA GibcoCel anion exchanger while maintaining the pH at 4.75 with 2 M sodium hydroxide. After mixing for 40 minutes the GMP depleted WPC was drained through a screen at the bottom of the vessel and the QA GibcoCel anion exchanger washed with water and drained.

The GMP was recovered from the anion exchanger as described in Example 2, except that 75 mM sodium chloride was used (pH 2) and then without any adjustment passed through a 100 mL column of cation exchanger (SP GibcoCel) as described in Example 2 to give 1.1 liters of GMP solution (column breakthrough plus wash water of 100 mL).

The GMP solution was divided into two fractions of 0.55 liters. The sodium chloride concentration in each of these was increased from 68 mM to 175 and 200 mM by the addition of 11.8 and 14.5 mL of 5 M sodium chloride, respectively. The solutions were then adjusted to pH 8.0 with 2 M sodium hydroxide and each passed through a 70 mL column of Q Sepharose® Fast Flow (Pharmacia)[a] which had been equilibrated to pH 8 in 175 mM and 200 mM sodium chloride respectively prior to packing. The flow rate was 5 mL/min. The last of the GMP solution was washed through the column with 70 mL of 175 mM and 200 mM sodium chloride respectively to give 0.62 liters of column breakthrough and washings. These were neutralized and samples dialysed and freeze-dried.

[a] Q Sepharose® Fast Flow is a strong anion exchanger with excellent flow properties and high capacity for proteins of all pI values. The ion exchange group is a quaternary amine which remains charged and maintains consistently high capacities over the entire working range, pH 2–12. Bead structure: 6% highly cross-linked agarose; bead size 45–165 micrometers.

The Phe analysis results from the GMP powders were as follows:

| | | |
|---|---|---|
| Initial Stage | | 0.68% Phe |
| Alternative i) | | 0.41% Phe |
| Alternative i) and iii) | using 200 mM NaCl | 0.21% Phe |
| | using 175 mM NaCl | 0.13% Phe |

Chromatography of the GMP products on a Mono Q® column showed that only the 0.13% Phe product was free of material eluting from the Mono Q® column after GMP (See Example 11). There were still traces of these impurities in the 0.21% Phe product.

EXAMPLE 6

This was the same as Example 5 except that alternative i), the intermediate cation exchange column (SP GibcoCel), was omitted. The two final GMP products from the Q Sepharose® Fast Flow columns gave Phe results of 0.41 and 0.32% respectively. Approximately 0.2% Phe can be attributed to the α-lactalbumin (3.7%) and β-lactoglobulin (1.8%) remaining in this type of product.

EXAMPLE 7

This was the same as Example 2 except that the GMP adsorption by the first anion exchanger (QA GibcoCel) was caffied out at pH 4.2 instead of 4.9. The 1 liter of GMP solution recovered at pH 2 and 100 mM NaCl (mostly glycosylated GMP) was divided into two 500 mL fractions.
(a) Purification through SP and QA Columns One 500 mL fraction was passed through a 40 mL column of SP GibcoCel cation exchanger over 2 hours and then adjusted to pH 8.5 and 175 mM sodium chloride and passed through a 40 mL column of QA GibcoCel anion exchanger as previously described.
(b) Purification through QA Column Only The other 500 mL fraction was adjusted to pH 8.5 and 175 mM sodium chloride and passed through a 40 mL column of QA GibcoCel anion exchanger.

Analyses of samples taken at the various stages gave the following results:

TABLE 4

Purity and Yield of GMP Products

| | Phe (%) | Yield[1] (%) | Yield[2] (%) | Sialic Acid (%) |
|---|---|---|---|---|
| Initial Stage GMP | 0.53 | 51.0 | 49.0 | — |
| Initial Stage GMP after: | | | | |
| Alternative i) only | 0.38 | 48.8 | 47.3 | — |
| Alternative iii) only | 0.22 | 45.0 | — | — |
| Alternative i) and iii) | 0.15 | 44.6 | — | 12.7 |

[1]Calculated from absorbance readings at 214 nm and using a value of 140 for a 1% solution of pure GMP.
[2]Analysis of GMP using a Mono S ® column. The load solution had a concentration of 14.2 mg GMP/mL.

EXAMPLE 8

GMP was adsorbed from 1 liter of 10% (w/w) reconstituted WPC (ALACEN 392™) at pH 4.8 by QA GibcoCel anion exchanger using the same techniques as in Example 2. The GMP was then desorbed from the drained and washed anion exchanger by a 2 stage elution as follows:

(a) Elution 1

Water was added to the anion exchanger to give a total volume of 1.1 liters. Aqueous sodium chloride (4 mL of 5 M) was added to make the solution approximately 20 mM, and the pH was lowered to 3.2. After stirring for 1 hour the desorbed GMP solution was drained from the anion exchanger which was washed with 20 mM sodium chloride to give 1 liter of recovered GMP, (mostly aglycomacropeptide). This was adjusted to pH 3.9 with 2 M sodium hydroxide and clarified by centrifugation. The supernatant (940 mL) was then passed (over 2 hours) through a 120 mL column of SP GibcoCel cation exchanger which had been pre-equilibrated at pH 3.9 in 20 mM sodium chloride. It was washed through with water to give 1.12 liters of column passed solution. A sample of this, and other GMP solutions from earlier in the process, were neutralized, dialysed and freeze-dried for Phe analyses. The results are shown in Table 4.

(b) Elution 2

After the first elution of protein from the QA GibcoCel anion exchanger it was again mixed with water to give a total volume of 1.1 liters. The sodium chloride was raised this time to approximately 200 mM by the addition of 20 mL of 5 M sodium chloride and the pH lowered to 3.0 to complete the recovery of GMP (mostly glycosylated) and other protein from the exchanger. After stirring for 1 hour the protein solution was drained from the exchanger and washed out with 200 mM sodium chloride to give 1 liter of recovered GMP. This was adjusted to pH 8.5 with 2 M sodium hydroxide and made up to 250 mM by the addition of a further 10 mL of 5 M sodium chloride. It was then passed through a pre-equilibrated column of QA GibcoCel anion exchanger (120 mL) over 2 hours and washed through with 250 mM sodium chloride to give 1.24 liters of solution. Samples were again taken for Phe analysis and the results are shown in Table 5.

TABLE 5

Purity and Yield of GMP Products

|  | Phe (%) | Yield (%)* | Sialic Acid (%) |
|---|---|---|---|
| Eluate 1 |  |  |  |
| Protein desorbed at pH 3.2/20 mM NaCl | 1.19 | 63 | 2.6 |
| Supernatant from pH 3.9 centrifugation | 0.98 | 55 | — |
| Breakthrough from SP GibcoCel column | 0.31 | 43 | 2.6 |
| Eluate 2 |  |  |  |
| Protein desorbed at pH 3.0/200 mM NaCl | 0.51 | 37 | — |
| Breakthrough from QA GibcoCel column | 0.28 | 33 | 17.4 |

*Yield of 214 nm absorbing material as a % of the total eluted, i.e. eluates 1 & 2 = 100%.

Example 9

(a) A WPC powder (ALACEN 392™) manufactured from cheese whey was reconstituted at 10% solids and the pH adjusted to 4.7 with 5 M hydrochloric acid. This solution (1 Kg) was mixed with 460 g (660 mL) of washed and drained QA GibcoCel anion exchanger whilst maintaining the pH at 4.7 with 2 M sodium hydroxide. After 40 minutes the GMP depleted WPC was drained through a screen at the bottom of the vessel and the retained ion exchanger washed with water.

The settled bed of QA GibcoCel anion exchanger was then washed with 1660 mL of 50 mM sodium chloride solution. Further 50 mM sodium chloride was then added to give a total volume in the vessel of 1 liter. This was stirred and the pH adjusted to 8.5–9.0 with 2 M sodium hydroxide. After about 10 minutes 35 mL of 5 M sodium chloride was added to raise the sodium chloride concentration from 50 to 175 mM to selectively elute the GMP. Mixing was continued for a further 30 minutes, whilst maintaining the pH at 8.5. The GMP containing eluate was then drained from the vessel and the bed of QA GibcoCel anion exchanger washed with 2 bed volumes (1320 mL) of 175 mM sodium chloride over 30 minutes to continue the elution of GMP. The total eluate (2 L), containing 71% of the GMP with 0.37% Phe, was concentrated by ultrafiltration, diafiltration and freeze-dried.

The QA GibcoCel was further treated to recover the remaining protein by adding water, adjusting the pH to 2.0 and mixing for a total time of 60 minutes. The eluted protein solution was drained and the ion exchanger washed with water.

(b) The above process was repeated except that the selective elution was carried out in 150 mM sodium chloride instead of 175 mM.

The GMP concentrations in the process streams at each stage were determined by analysis on a Mono S® column to determine the losses and yield of GMP. These results along with those from amino acid analyses on the final products are shown in Table 6.

TABLE 6

Purity and Yield of GMP

|  |  | Yield (%)* | Phe % |
|---|---|---|---|
| GMP depleted WPC and wash |  | 13 | — |
| Salt wash |  | 4 | — |
| Selective elusions |  |  |  |
| (a) (i) pH 8.5/175 mM NaCl |  | 71 | 0.37 |
| (ii) pH 2.0/.100 mM NaCl |  | 14 | 1.9 |
| (b) pH 8.5/150 mM NaCl |  | 58 | 0.26 |

*Based on the GMP present in the reconstituted WPC.

EXAMPLE 10

A WPC powder (ALACEN 392™) manufactured from cheese whey was reconstituted at 7.5% solids. The pH of this was adjusted to 4.75 with 5 M hydrochloric acid and 1 Kg of it mixed with 350 g (500 mL) of washed and drained QA GibcoCel anion exchanger while maintaining the pH at 4.75 with 2 M sodium hydroxide. After mixing for 40 minutes the GMP-depleted WPC was drained through a screen at the bottom of the vessel and the retained ion exchanger washed with water. The bed of QA GibcoCel anion exchanger was then washed with 1250 mL of 50 mM sodium chloride solution to desorb mainly contaminating proteins. This was followed by a water wash of 250 mL which was drained completely from the ion exchange bed.

Water was added to the GMP loaded QA GibcoCel anion exchanger to give a total weight of 750 g. Sodium chloride (9 mL of 5 M) was added to make the solution approximately 60 mM, and the pH was then lowered to 2.0 with 5 M hydrochloric acid. This was mixed for 1 hour at room temperature. The eluted protein was drained from the bed of exchanger which was then washed with water to give 900 mL of GMP solution with a sodium chloride concentration of 50 mM and about pH 2. This was neutralized to pH 9 with 2 M sodium hydroxide and divided in two equal fractions.

(a) Half the GMP solution (450 mL) was made up to 150 mM sodium chloride by the addition of a further 9 mL of 5 M sodium chloride and passed through a 50 mL column of QA GibcoCel anion exchanger pre-equilibrated to pH 9 in 150 mM sodium chloride prior to packing as a column. A flow rate of 4 mL/min was used. The last of the GMP solution was flushed through the column with 50 mL of 150 mM sodium chloride to give 500 mL of purified GMP which was neutralized.

(b) The other half of the GMP solution (450 mL) was left at 50 mM sodium chloride strength and passed at 4 mL/min through a 50 mL column of DMO cellulose[1] pre-equilibrated to pH 9 in 50 mM sodium chloride prior to packing as a column. Fifty milliliters of 50 mM sodium chloride was used to flush the last of the GMP solution through the column to give 500 mL of purified GMP solution.

[1] DMO cellulose was a dimethyloctylamino cellulose prepared in the laboratory from HP GibcoCel using the method of L Matsumoto et al., J. Biochem. 87, 535–540 (1980) to prepare an epoxy-activated cellulose. This was then coupled with N,N-dimethyloctylamine in aqueous ethanol to give DMO cellulose with a substitution level of 0.8 meq/g (55 ueq/mL).

Small samples of GMP containing solutions were kept for GMP analysis by ion exchange on a Mono S® column or dialysed, freeze-dried and hydrolysed for phenylalanine analysis by amino acid assays. The results are shown in Table 7.

TABLE 7

Purity and Yield of GMP

|   | Yield (%)* | Phe % |
|---|---|---|
| GMP depleted WPC and wash. | 5.0 | — |
| Salt wash. | 5.5 | — |
| Initial Stage | 82 | 0.76 |
| Alternative (iii) using |   |   |
| (a) QA GibcoCel anion exchanger in 150 mM NaCl | 71 | 0.40 |
| (b) DMO Cellulose in 50 mM NaCl | 71 | 0.28 |

*Based on the GMP present in the reconstituted WPC.

EXAMPLE 11

Cheese whey WPC powder was reconstituted to give 2 liters of a 10% (w/w) solution. This was heat treated to precipitate the whey proteins except for GMP and centrifuged at 90° C. One liter of the GMP containing supernatant was then adjusted to pH 4.8 and treated with 660 mL of QA GibcoCel anion exchanger and the GMP obtained further purified as described in Example 3. Samples (10 mL) were taken at each stage, neutralized, dialysed and freeze-dried. Phe analyses gave the following results:

|   |   | Phe % |
|---|---|---|
| Supernatant from heat treated WPC |   | 2.15 |
| Initial Stage | Protein desorbed from QA GibcoCel column | 1.03 |
| Alternative i) | Breakthrough from SP GibcoCel column | 0.34 |
| Alternative i) and iii) | Breakthrough from QA GibcoCel column | 0.31 |

EXAMPLE 12

Most of the GMP samples produced in the proceeding examples were analysed by anion exchange chromatography using a Mono Q® PC 1.6/5 column coupled to a Pharmacia SMART™ System. Samples (2 mg/mL) were dissolved in 0.01 Tris buffer at pH 8.0. The Mono Q® column was equilibrated and run under the following conditions using: Buffer A: 0.01 M Tris, pH 8.0 and Buffer B: 001 M Tris, 1 M NaCl, pH 8.0.

TABLE 8

Gradient Table

| Time min | Flow: L/min | % A | % B |
|---|---|---|---|
| 0 | 80 | 90 | 10 |
| 12.5 | 80 | 72 | 28 |
| 18.0 | 80 | 50 | 50 |
| 20.0 | 80 | 0 | 100 |
| 23.0 | 80 | 0 | 100 |
| 26.0 | 80 | 90 | 10 |
| 31.0 | 0 | 90 | 10 |

Figure 3:
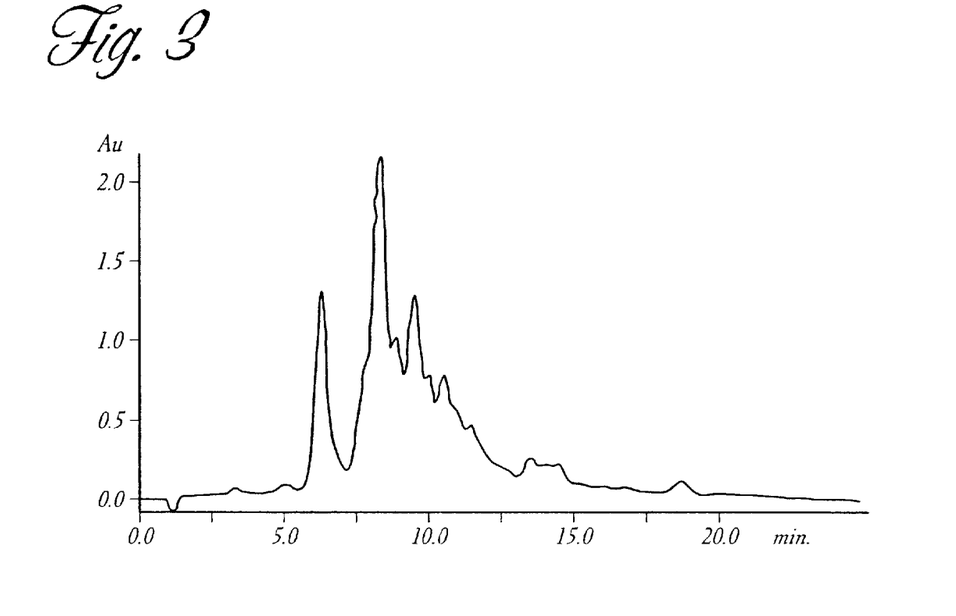
FIG. 3 is a plot of time against the absorbance at 214 nm of proteinaceous material eluting off a Mono Q® column at pH 8 with an increasing sodium chloride gradient for GMP containing impurities.

FIG. 3 shows a typical chromatogram obtained for the GMP samples obtained in alternative i) of the process as set out in Examples 2 and 3, i.e. the protein desorbed from the QA GibcoCel anion exchanger and passed through the SP GibcoCel column at pH 2.

The peaks eluting between 4 and 13 minutes were mainly GMP, i.e. the A and B variants of the aglyco and variously glycosylated forms of the macropeptide obtained from δ-casein. The peaks eluting after 13 minutes were not GMP and these impurities gave rise to significant levels of Phe in the GMP obtained from a single stage extraction of GMP from cheese and rennet casein wheys and retentates by ion exchange. When α-lactalbumin, BSA, β-lactoglobulin and these other impurities were removed from the GMP by a multistage process, such that they were no longer detectable by chromatography on a Mono Q® column, then GMP was obtained with <0.2% Phe in its amino acid composition. Complete removal of the peaks eluting between 13 and 15 minutes was not always achieved resulting in products with 0.2 to 0.4% Phe. Such products have been readily obtained on a 200 liter scale using GibcoCel exchangers with retentates and reconstituted WPC powders from rennet casein whey and various kinds of cheese wheys. The distribution and size of the peaks in the 13–15 minute range varied with different whey types but the bulk of them were removed by the processes set out in these examples so that the Phe content of the final product was not affected by these differences.

EXAMPLE 13

This was the same as Example 3 except that the semi-purified GMP, obtained after passage of the GMP through the SP GibcoCel column at pH 2 in 75 mM sodium chloride, was heated for 20 minutes at 80° C. to hydrolyse the sialic acids groups off the various glyco forms of the macropeptide.

After cooling, 3×360 mL fractions of this hydrolysed solution were made up to 125, 150 and 175 mM in sodium chloride by the addition of 4, 5.8 and 7.6 mL of 5 M sodium chloride respectively. Each of these fractions was then adjusted to pH 8.0 and passed through a 40 mL column of QA GibcoCel anion exchanger previously adjusted to pH 8.0 in 125, 150 or 175 mM sodium chloride prior to settling as a column. The flow rate was 3 mL/min. The last of each GMP solution was flushed through the column with the appropriate strength of sodium chloride to give 400 mL of purified GMP solution. Samples of each solution were diluted 1 in 100 with water and the absorbance at 214 nm measured to estimate the GMP concentration using a value of 140 for the absorbance of a 1% solution of pure GMP at 214 nm. The results in Table 3 validate this method of analysis for very pure samples of GMP. Other samples were neutralized, dialysed and freeze-dried for Phe analysis.

Figure 4:
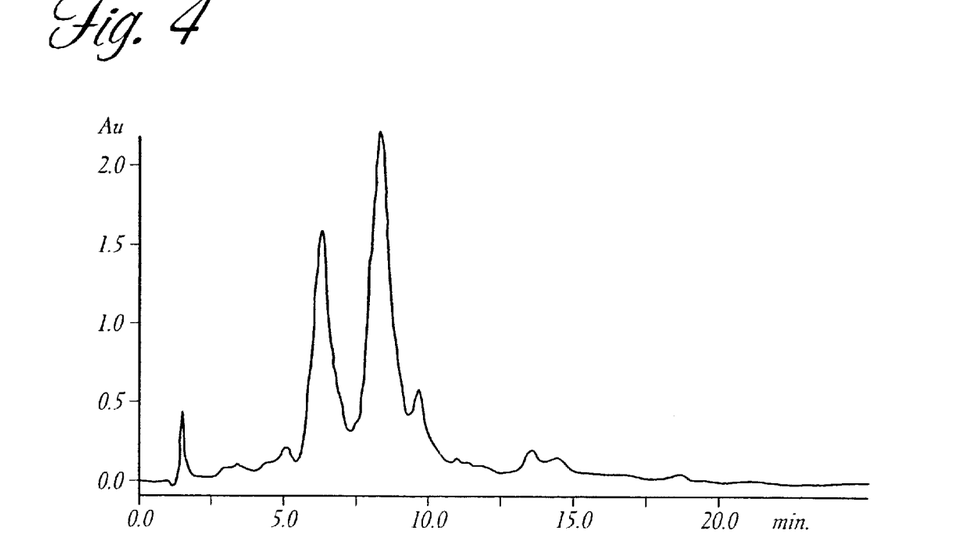
FIG. 4 is the same plot as FIG. 3 but for GMP after most of its sialic acid groups have been removed by hydrolysis.

FIG. 4 shows the Mono Q® chromatogram for this hydrolysed GMP and the very large separation now between the two main asialyo GMP peaks and the Phe containing impurities at 13–15 minutes. This made it possible to use lower salt strengths for the QA GibcoCel column to bind these impurities in alternative iii) without also binding the GMP. The results in Table 9 show that the sodium chloride concentration in the range 125–175 mM is not particularly critical to the performance of the anion exchange column used in this alternative of the process.

TABLE 9

|  | Phe % | yield %[1] | sialic acid %[2] |
|---|---|---|---|
| GMP from initial stage | 1.0 | — | — |
| Hydrolysed GMP from alternative i) | 0.48 | — | — |
| GMP from 175 mM NaCl QA GibcoCel column | 0.20 | 74 | — |
| GMP from 150 mM NaCl QA GibcoCel column | 0.14 | 70 | 1.2 |
| GMP from 125 mM NaCl QA GibcoCel column | 0.16 | 66 | — |

[1]Yield of the GMP that was present in the WPC at the start.
[2]The final GMP obtained in Example 2 (no hydrolysis) had a sialic acid content of 5.4%.

EXAMPLE 14

A WPC powder (ALACEN 392™) manufactured from cheese whey was reconstituted in demineralised water at 15%(w/v) solids to give 1700 L of reconstituted retentate. The pH of this retentate was adjusted to pH 4.75 with 29 L of 10% HCl and 160 L of it mixed with 150 L of anion exchanger (QA GibcoCel) in a bed of water. The pH was maintained at 4.75 whilst continuing this mixing for 30 minutes at 10° in a vessel fitted with a stirrer and a screen across the bottom. At the end of the mixing period the GMP-depleted retentate was drained from the anion exchanger which was then washed with water.

Demineralised water was added to the washed anion exchanger to give a total volume of 300 L. Cheese salt was added to make the solution approximately 55 mM in sodium chloride and the pH was lowered to 2.0 with 10% HCl. This was mixed for 1 hour at 10° C. to desorb the GMP and other protein from the exchanger and then the exchanger was drained and washed to give 250 L of eluate and washings. Nine further cycles were carried out in this manner to give a total of 2500 L of GMP eluate.

The GMP eluate, at pH 2.0 and 55 mM sodium chloride, was passed at 250 L/hr and 10° C. through a column containing 80 L of cation exchanger (SP GibcoCel) which had been previously stirred and adjusted to pH 2 prior to settling as a column. The eluate was flushed through the column with 80 L of water.

The GMP solution that had passed through the cation exchanger was made 175 mM in sodium chloride by the addition of 11 kg of sodium chloride and then the pH was adjusted to pH 8.5 with 10% sodium hydroxide. This was then passed at 475 L/hr and 10° C. through 150 L of QA GibcoCel anion exchanger which had been previously stirred in 175 mM sodium chloride and adjusted to pH 8.5 prior to settling and packing as a column. The last of the GMP solution was flushed through the column with 175 mM sodium chloride.

The GMP solution (2800 L) that had passed through the anion exchanger was neutralised to pH 6.7 with 1.3 L of 10% HCl. It was then ultrafiltered at 10° C. in batch mode to VCF 15 using two 4" diameter Koch HFK328 UF membranes. Three diafiltration steps, each of VCF 2, were then carried out after which the permeate conductivity was 2 mS. A final concentration stage was then carried out to lift the retentate refractive index to 16°Br.

The GMP retentate (150 L) was spray dried on an Anhydro Integral Fluid Bed drier to give 26 kg of powder containing 82.6% protein (dry basis). The Phe content of the powder was 0.24% of protein.

INDUSTRIAL APPLICABILITY

The process of the present invention is capable of being applied to the mass production of GMP having a Phe content of not greater than about 0.5% (w/w), such purified GMP being suitable for use in the manufacture of low Phe diets for PKU patients.

What is claimed is:

1. A process for the purification of glycomacropeptide (GMP), comprising:
   contacting a feedstock containing GMP with a first anion exchanger under conditions to adsorb said GMP;
   obtaining an eluate containing GMP by eluting said adsorbed GMP from said anion exchanger with an eluent;
   removing impurities from said eluate containing GMP, wherein said impurities comprise other whey proteins, by a technique selected from the group consisting of:
   a) contacting said eluate containing GMP with a cation exchanger in conditions under which said impurities in said eluate are adsorbed onto said cation exchanger, and precipitating said impurities in said eluate containing GMP using conditions by means of which said GMP remains in solution,
   b) precipitating said impurities in said eluate containing GMP using conditions by means of which said GMP remains in solution,
   c) contacting said eluate containing GMP with a second anion exchanger in conditions under which said impurities in said eluate are adsorbed onto said anion exchanger, and
   d) contacting said eluate containing GMP with a cation exchanger in conditions under which said impurities in said eluate are adsorbed onto said cation exchanger, and contacting said eluate containing GMP with a second anion exchanger in conditions under which said impurities in said eluate are adsorbed onto said anion exchanger; and
   recovering a purified GMP, wherein said purified GMP has an amino acid composition containing not greater than 0.5% (w/w) phenylalanine.

2. The process according to claim 1 wherein said conditions in said first anion exchanger are such that said GMP is adsorbed selectively.

3. The process according to claim 1 wherein said conditions in said first anion exchanger are such that both said GMP and said other whey proteins in said feedstock are adsorbed on said first anion exchanger and eluted under conditions which selectively elute said whey proteins and then elute said GMP.

4. The process according to claim 1, wherein said conditions for eluting said impurities are obtained by adjusting said first anion exchanger to a pH of about 4 to about 5 and using about 20 to about 60 mM sodium chloride as the eluent.

5. The process according to claim 1, wherein said feedstock is derived from a casein or caseinate product prepared by acid precipitation and has been further treated with a suitable enzyme to release the GMP into said feedstock and precipitate casein.

6. The process according to claim 1, wherein said eluate containing GMP from said first anion exchanger is treated with said technique (a).

7. The process according to claim 1, wherein said eluate containing GMP from said first anionic exchanger is treated with said technique (b).

8. The process according to claim 1, wherein said eluate containing GMP from said first anionic exchanger is treated with said technique (c).

9. The process according to claim 1, wherein said eluate containing GMP from said first anionic exchanger is treated with said technique (d).

10. The process according to claim 1, wherein said eluent for desorbing said GMP from said first anion exchanger contains salt in a sufficient quantity to make the solution about 175 mM and base in sufficient quantity to raise the pH of a range of about 8 to about 9.

11. The process according to claim 1, wherein said eluate containing GMP in technique (a) is contacted with said cation exchanger, wherein said eluate containing GMP has a pH of about 1.5 to about 4.5 and at a salt concentration of up to 100 mM.

12. The process according to claim 1, wherein said eluate containing GMP in technique (d) is contacted with said cation exchanger, wherein said eluate containing GMP has a pH of about 1.5 to about 4.5 and has a salt concentration of up to 100 mM.

13. The process according to claim 1, wherein said purified GMP is neutralized and concentrated by a process selected from the group consisting of ultrafiltration, diafiltration, and a combination thereof, prior to drying.

14. The process according to claim 1, wherein after precipitation said impurities in said eluate containing GMP, said eluate is centrifuged or microfiltered to obtain a supernatant or a permeate, and the supernatant or permeate is further processed by contacting said supernatant or permeate with a cation exchanger or is immediately neutralized, concentrated and dried to produce a GMP powder.

15. The process according to claim 1, wherein the process is conducted under conditions which promote a high yield.

16. Purified GMP wherein the GMP is purified to contain no more than 0.5% w/w of phenylalanine when prepared by a process as claimed in claim 1.

17. Purified GMP wherein the GMP is purified to contain no more than 0.4% w/w of phenylalanine when prepared by a process as claimed in claim 1.

18. The process according to claim 1, wherein said feedstock containing GMP is contacted with said first anionic exchanger at a pH of about 3 to about 9.

19. The process according to claim 18, wherein said pH is about 3.5 to about 5.

20. The process according to claim 1, wherein said eluent for eluting said GMP from said first anionic exchanger contains salt in a sufficient quantity to make a solution of about 20 to about 200 mM and acid in a sufficient quantity to lower pH of said eluent of a range of about 2 to about 3.

21. The process according to claim 20, wherein said salt is sodium chloride.

22. The process according to claim 1, wherein after the initial step of contacting said first anion exchanger with said feedstock containing GMP, said first anion exchanger is washed at a pH of about 4 to about 5 with a dilute salt solution prior to GMP elution.

23. The process according to claim 22, wherein the dilute salt solution is about 50 mM sodium chloride.

24. The process according to claim 1, wherein in said techniques (a) and (b) said conditions are pH of about 3.5 to about 4.5 attained by adding an acid or a base to the eluate containing GMP.

25. The process according to claim 24, wherein said acid is hydrochloric acid.

26. The process according to claim 24, wherein said base is sodium hydroxide.

27. The process according to claim 1, wherein said techniques (c) and (d), said second anion exchanger is substituted with amino groups bearing at least one hydrophobic group.

28. The process according to claim 27, wherein said at least one hydrophobic group is selected from the group consisting of aliphatic $C_6$–$C_{12}$ hydrocarbon groups and aromatic $C_6$–$C_{12}$ hydrocarbon groups.

29. The process according to claim 28, wherein said hydrophobic group is a $C_8$ hydrocarbon group.

30. The process according to claim 1, wherein said feedstock containing GMP is selected from the group consisting of: a cheese whey, a rennet whey, an ultrafiltrate retentate, and a whey protein isolate produced from cheese whey or rennet whey by an anion exchanger or microfiltration.

31. The process according to claim 30, wherein said feedstock has been pretreated to remove substantially all the whey proteins contained therein except the GMP.

32. The process according to claim 31 wherein said whey proteins have been substantially removed by heat treating said feedstock.

33. The process according to claim 31 wherein said whey proteins have been substantially removed by contacting the feedstock with a cation exchanger.

34. A process for the purification of GMP, comprising:

contacting a feedstock containing GMP with an anion exchanger under conditions to adsorb selectively said GMP, eluting selectively said adsorbed GMP from said anion exchanger leaving impurities on said anion exchanger, and recovering an eluate containing a purified GMP, wherein said purified GMP has a phenylalanine content of not greater than 0.5% (w/w).

35. The process according to claim 34, wherein said GMP is selectively eluted at a pH of about 4 or more.

36. The process according to claim 34, wherein said said anion exchanger is regenerated by eluting said impurities therefrom after said GMP elution.

37. The process according to claim 34, wherein said GMP is selectively eluted with an eluent having a pH of about 8 to about 9 and additionally having a salt concentration of about 175 mM.

38. The process according to claim 34, wherein the GMP is selectively adsorbed onto said anion exchanger at a pH of about 5 or less.

39. The process according to claim 38, wherein said GMP is selectively adsorbed at a pH of about 4 to about 5.

40. The process according to claim 34, wherein prior to said eluting of adsorbed GMP said anion exchanger with adsorbed GMP is washed with a dilute salt solution to remove impurities therefrom.

41. The process according to claim 40, wherein said dilute salt solution is about 50 mM sodium chloride.

42. The process according to claim 34, wherein said GMP is selectively eluted with an eluent comprising a salt solution having a concentration of about 50 to about 250 mM.

43. The process according to claim 42, wherein said GMP is selectively eluted with an eluent comprising a salt solution having a concentration of about 50 to about 175 mM.

* * * * *

UNITED STATES PATENT AND TRADEMARK OFFICE
CERTIFICATE OF CORRECTION

PATENT NO. : 6,555,659 B1
DATED : April 29, 2003
INVENTOR(S) : John Stephen Ayers et al.

It is certified that error appears in the above-identified patent and that said Letters Patent is hereby corrected as shown below:

Column 6,
Line 9, "are" should be -- art --.

Column 7,
Line 51, "110º C. for 23 hours and 110º C. analysed" should be -- 110º C for 23 hours and analysed".

Column 8,
Line 66, "nmL" should be -- mL --.

Column 10,
Line 46, "50EC" should be -- 50ºC --.

Column 12,
Line 13, "Example 11" should be -- Example 12 --.
Line 29, "caffied" should be -- carried --.

Column 16,
Line 27, "6-casein" should be -- κ-casein -- (the Greek letter kappa).

Signed and Sealed this

Fourteenth Day of October, 2003

JAMES E. ROGAN
*Director of the United States Patent and Trademark Office*